United States Patent
Kampas et al.

(10) Patent No.: US 9,161,847 B2
(45) Date of Patent: Oct. 20, 2015

(54) ORTHOPEDIC DEVICE COMPRISING A JOINT

(75) Inventors: Philipp Kampas, Vienna (AT); Roland Pawlik, Vienna (AT)

(73) Assignee: OTTO BOCK HEALTHCARE PRODUCTS GMBH, Vienna (AT)

(*) Notice: Subject to any disclaimer, the term of this patent is extended or adjusted under 35 U.S.C. 154(b) by 236 days.

(21) Appl. No.: 12/993,786

(22) PCT Filed: May 19, 2009

(86) PCT No.: PCT/EP2009/003562
§ 371 (c)(1),
(2), (4) Date: Feb. 14, 2011

(87) PCT Pub. No.: WO2009/141115
PCT Pub. Date: Nov. 26, 2009

(65) Prior Publication Data
US 2011/0130846 A1    Jun. 2, 2011

(30) Foreign Application Priority Data

May 20, 2008 (DE) .......................... 10 2008 024 747

(51) Int. Cl.
*A61F 2/64* (2006.01)
*A61F 2/68* (2006.01)
(Continued)

(52) U.S. Cl.
CPC ... *A61F 2/68* (2013.01); *A61F 2/64* (2013.01);
*A61F 2002/5006* (2013.01); *A61F 2002/689* (2013.01); *A61F 2002/6854* (2013.01);
(Continued)

(58) Field of Classification Search
CPC .............................................. A61F 2002/6854

USPC .......... 623/24, 25, 26, 27, 39, 43, 44, 45, 46; 606/16, 23, 26
See application file for complete search history.

(56) References Cited

U.S. PATENT DOCUMENTS 4,034,419 A * 7/1977 Roberts .......................... 623/43
5,383,939 A    1/1995 James
(Continued)

FOREIGN PATENT DOCUMENTS

DE    69209476 T2    1/1997
DE    19752184 A1    5/1999
(Continued)

OTHER PUBLICATIONS

Martin, Craig; Otto Bock C-leg: A review of its effectiveness; Nov. 27, 2003; WCB Evidence Based Group, pp. All.*
(Continued)

*Primary Examiner* — Marcia Watkins
(74) *Attorney, Agent, or Firm* — Holland & Hart

(57) ABSTRACT

The application relates to an orthopedic device comprising a joint and to a method for controlling an orthopedic device, which has an upper part (1) and a lower part (2) supported pivotally thereon, wherein upper connecting means for fixation onto a limb are disposed on the upper part (1), and a locking device (3), which prevents a bending motion of the upper part (1) relative to the lower part (2), wherein the locking device (3) is configured such that it can be actively actuated by the user of the orthopedic device, wherein a control device (9) is associated with the locking device (3), the control device being attached to the device with at least one sensor (6, 7, 8) and automatically unlocking or locking the locking device (3) as a function of the sensor signal.

21 Claims, 1 Drawing Sheet

(51) Int. Cl.
A61F 2/50 (2006.01)
A61F 2/76 (2006.01)
A61F 2/70 (2006.01)
A61F 2/74 (2006.01)

(52) U.S. Cl.
CPC ..... *A61F2002/704* (2013.01); *A61F 2002/707* (2013.01); *A61F 2002/741* (2013.01); *A61F 2002/745* (2013.01); *A61F 2002/748* (2013.01); *A61F 2002/763* (2013.01); *A61F 2002/769* (2013.01); *A61F 2002/7625* (2013.01); *A61F 2002/7635* (2013.01); *A61F 2002/7645* (2013.01)

(56) References Cited

U.S. PATENT DOCUMENTS

| | | | |
|---|---|---|---|
| 5,779,735 | A | 7/1998 | Molino |
| 6,517,585 | B1 * | 2/2003 | Zahedi et al. .................. 623/24 |
| 6,755,870 | B1 | 6/2004 | Biedermann et al. |
| 6,908,488 | B2 | 6/2005 | Passivaara et al. |
| 7,172,567 | B2 | 2/2007 | Lidolt et al. |
| 2004/0225242 | A1 | 11/2004 | Lidolt et al. |
| 2007/0083272 | A1 | 4/2007 | Van De Veen et al. |
| 2010/0191347 | A1 | 7/2010 | Pusch et al. |

FOREIGN PATENT DOCUMENTS

| | | |
|---|---|---|
| DE | 19859931 A1 | 7/2000 |
| DE | 10311187 A1 | 10/2004 |
| DE | 10311189 B4 | 10/2004 |
| DE | 10351916 A1 | 6/2005 |
| DE | 60015384 T2 | 10/2005 |
| DE | 102007032090 A1 | 1/2009 |
| EP | 1237513 B1 | 10/2004 |
| WO | 0078263 A2 | 12/2000 |
| WO | 0143669 A1 | 6/2001 |
| WO | 03086245 A2 | 10/2003 |
| WO | 2007027668 A2 | 3/2007 |
| WO | 2008044207 A2 | 4/2008 |
| WO | 2008048658 A2 | 4/2008 |
| WO | 2008080231 A1 | 7/2008 |

OTHER PUBLICATIONS

Quick Guide #3; C-Leg Patient Training Overview, Otto Bock, 2006, Training Pamphlet, pp. 1-4.*
Authors: Numerous (compilation of articles); International C-Leg Studies 3rd Edition; Various Dates from 1998 thru 2009; Otto Bock; pp. 1-52.*
PCT International Search Report for International Application No. PCT/EP2009/003562, mailed Sep. 10, 2009.

* cited by examiner

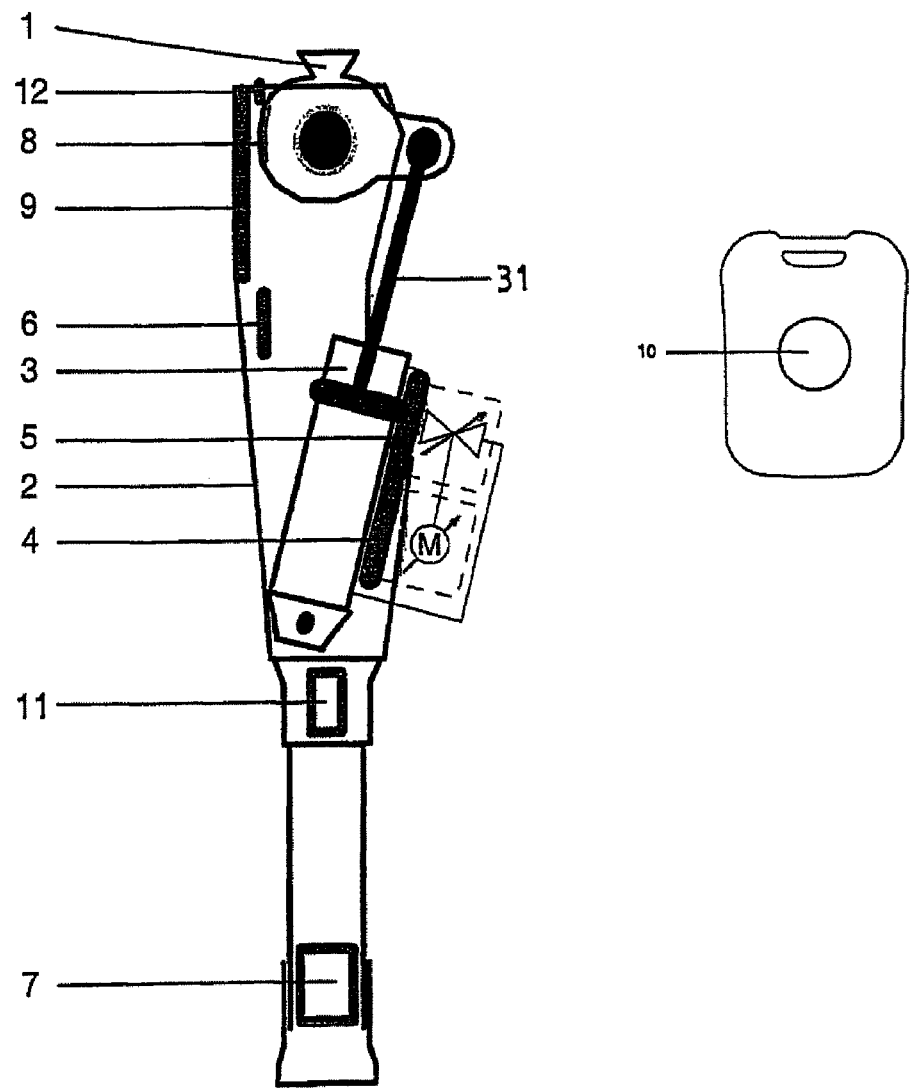

ORTHOPEDIC DEVICE COMPRISING A JOINT

TECHNICAL FIELD

The invention relates to an orthopedic device with a joint, which device has an upper part and a lower part mounted thereon such that it can pivot, wherein upper connection means for attachment to a limb are arranged on the upper part, and which device also has a locking device that prevents a bending movement of the upper part relative to the lower part, wherein the locking device is embodied such that it can actively be actuated by the user of the orthopedic device. The invention likewise relates to a method for controlling an orthopedic device. In particular, such orthopedic devices are used as orthoses or prostheses, preferably as knee joint orthoses or prosthetic knee joints.

BACKGROUND

Orthopedic devices with two parts that can move relative to one another and with a locking device arranged therebetween for locking the two parts in a predetermined relative position and for unlocking the parts to allow the movement of the parts with respect to one another are used in a number of applications for compensating temporary or permanent weaknesses in the human body or for allowing functions that otherwise cannot be exercised. When caring for patients with a low degree of mobility, that is to say patients that mainly stay indoors and sometimes have reduced muscular and motor abilities, that is to say in the case of so-called geriatric patients, orthopedic devices are often designed with a blocking joint, wherein such apparatuses are used in particular to support the function of the leg. Thus, knee orthoses or prosthetic knee joints can for example be used as blocking joints that are automatically locked as a result of a blocking mechanism when they are fully extended and have to be unlocked manually for bending. In the case of knee joints, a blocked knee joint, be it a prosthesis or an orthosis, is the safest configuration for standing and walking. Protection from falls is an important object, particularly when caring for geriatric patients, wherein the unlocking is predominantly brought about by pulling a pulling cable, which is laid from the knee joint up to the upper thigh such that the pulling cable can easily be reached when standing. Thus, standing and walking is performed with a stiff knee joint, whilst sitting is performed with a bent, freely movable knee joint provided the knee joint is not fully extended when seated.

DE 103 11 187 A1 describes an orthopedic-technical aid with a locking apparatus for locking and unlocking two parts mounted movably with respect to one another, wherein the locking apparatus can be actuated electromechanically by a control module and an actuation signal is transferred wirelessly onto the control module from an actuation unit. The actuation unit can be integrated into a walking aid, and so the locking apparatus can be unlocked by means of a remote control.

DE 103 51 916 A1 describes a prosthetic knee joint for geriatric patients, which has been provided with a hydraulic damping unit that can be operated as a locking device. Bending of the joint device is blocked within a fixed angular range, wherein the lower part can be freely pivoted in the bending direction outside of the angular range that can be fixed. Extending the lower part should be possible at all times. Such a prosthetic knee joint is used as an aid for standing up and sitting down.

EP 1 237 513 B1 relates to the existence or function of a support apparatus that replaces limbs and comprises a sensor, wherein the sensor detects the position relative to a fixed line of an element connected to a joint, wherein the sensor is coupled to a control apparatus that is provided for controlling the joint on the basis of the positional data from the sensor. In its simplest form, the apparatus for controlling the knee joint is a locking or braking apparatus.

SUMMARY

An object of the present invention is to provide an orthopedic device and a method for controlling an orthopedic device, by means of which a higher degree of comfort can be obtained with adequate safety whilst walking and standing.

According to the invention, this object is achieved by an orthopedic device with the features of the main claim and a method with the features of claim 10 for controlling such an orthopedic device. Advantageous embodiments and developments of the invention are described in the dependent claims.

The orthopedic device according to the invention with a joint, which device has an upper part and a lower part mounted thereon such that it can pivot, wherein upper connection means for attachment to a limb are arranged on the upper part, and which device also has a locking device that prevents a bending movement of the upper part relative to the lower part, wherein the locking device is embodied such that it can actively be actuated by the user of the orthopedic device, provides for a control device to be associated with the locking device, to be connected to at least one sensor attached to the device, and to unlock or block the locking device as a function of the sensor signal in an automatic fashion. While conventional orthopedic devices, more particularly prosthetic knee joints or knee joint orthoses, require an active release of a locking device in order to bend the joint, the orthopedic device according to the invention provides for the joint device to be also unlocked or blocked involuntarily as a function of sensor information provided by sensors arranged on the orthopedic device in addition to a voluntary locking or unlocking of said joint device. In addition to voluntary activation of the locking and unlocking device, it is possible to undertake an automated release of a block or a reduction in resistance of the joint as a function of the position of the upper part or the lower part or of other parameters such that use is eased, particularly for users with reduced motor abilities. Hence, in respect of prosthetic knee joints, it is therefore possible for a user with a locked joint to be able to sit down without having to actively unblock the locking device, wherein the joint is unblocked automatically when a prescribed orientation of the upper part and/or the lower part is reached, and so there is free mobility when seated. Furthermore, the joint is prevented from locking when seated if the leg is completely extended, the latter being a hindrance when the prosthesis wearer is in the seated position. A corresponding application is also possible for joint orthoses, wherein attachment devices for attachment to a limb, for example to the shank or the forearm, are provided on the lower part in this case. In the case of an embodiment of the orthopedic device as a prosthesis joint, provision is made for attaching further orthopedic or prosthetic components to the lower part.

A development of the invention provides for the sensor to be coupled to the control device and designed as a position sensor for registering the orientation of the upper part and/or the lower part in space, as an angle sensor for registering the angle between the upper part and the lower part, as a force sensor for registering a force acting in the orthopedic device and/or as a torque sensor for registering a torque acting in the orthopedic device. By way of example, detecting the change in angle between upper part and lower part from the rotational direction in conjunction with the absolute position of the upper part and the lower part allows conclusions to be drawn as to whether a patient wishes to stand up, and so the joint can already be blocked automatically before the knee is fully extended when standing up. The blocking can also be effected in one direction only, and so the extension is always possible but bending can already be prohibited in a first phase of standing up in order to avoid the patient falling back unintentionally while they are standing up. By way of example, this allows blocking of a knee joint whilst standing up when the extension is only reached approximately, for example 15° before reaching an extension stop when the shank is aligned approximately vertically. In addition to taking the angle between the upper part and the lower part into account, a sensor for registering the orientation of the upper part and/or the lower part in space can be provided in order to be able to bring about automatic unlocking or blocking of the locking device by itself or in conjunction with the angle sensor data. In the case of a horizontal orientation of the upper part in an embodiment as a prosthetic knee joint, this allows the conclusion to be drawn that the user is in a seated position if the upper part is substantially oriented horizontally and, at the same time, there is an approximate right angle between upper part and lower part, and so automatic unlocking takes place. A force or torque sensor for determining the force acting in the orthopedic device or for determining the torque acting in the orthopedic device can also be formed, wherein the force and/or torque sensors can likewise be used to supplement the angle sensor or the position sensor. A force sensor for registering a force, more particularly an axial force, acting in the lower part is preferably arranged in the lower part and connected to the control device. This affords the possibility of detecting whether a load is exerted on the lower part, for example, or whether or not a patient is standing and exerting a load on the orthopedic device, more particularly the prosthesis. Thus blocking can be dispensed with when seated in the case of no axial load being present or only a very small axial load being present when the lower part has a vertical orientation, whereas blocking in the bending direction can be initiated in the case of an axial load, for example whilst standing or standing up, in order to prevent the patient from falling back. This also prevents the joint from locking whilst seated if the leg or the prosthesis is extended fully but at the same time no axial load is detected acting in the lower part. Provision can be made for a joint torque sensor for registering the torque acting in the joint between upper part and lower part, with the joint torque sensor likewise being connected to the control device. Further information relating to the forces acting within the orthopedic device can be determined by the joint torque sensor, and so the control can be brought about in a more precise fashion.

The orthopedic device is preferably designed as an orthotic knee joint or as a prosthetic knee joint, but in principle the application as for example an elbow orthesis or forearm prosthesis is also provided.

The locking device is preferably a hydraulic damper, which has at least one valve that can be switched by an actuator or one restrictor that can be switched by an actuator, wherein the actuator is connected to the control device. This affords the possibility of increasing or reducing the hydraulic damping in order to lock a joint if a corresponding valve is completely closed or to provide a desired damping resistance if a valve or a restriction is opened or closed to a certain extent.

A development of the invention provides for a timing switching element to be associated with the control device, the former delaying unlocking or locking or blocks the unlocking device only after an appropriate sensor signal. This timing switching element affords the possibility of allowing a multiplicity of control variants, for example keeping the locking device open in a time-controlled fashion after automatic unlocking or a time-controlled relocking after unlocking by means of the control signal. It is likewise possible for relocking to be impossible for a certain amount of time after voluntary unlocking such that the patient has sufficient time after unlocking for example to obtain an additional hold and to sit down. Likewise, there can be automatic relocking after a certain amount of time has passed after voluntary unlocking provided that the sensor signal or the sensor signals do not register an unlocking, that is to say a use after unlocking, and so the assumption can be made that the user has forgotten about the unlocking. Hence automatic locking is initiated for safety reasons.

A damping element can be associated with the orthopedic device and acts on the actuator such that unlocking is brought about in a continuous fashion, i.e. the valves or restrictions are only opened slowly and not abruptly when unlocking, and so there is no immediate unlocking that would constitute insecurity for most users.

The embodiment of the locking device as a hydraulic damper can also be designed such that the hydraulic damper allows damped bending from an extension stop to a fixed bending angle, while further bending is blocked once the fixed bending angle has been reached. This can be brought about by a mechanical control that allows play within the locking device, for example by keeping open a bypass line over a range of 5° to 10° from the extension stop, which bypass line is closed by a control disk or the like once this bending angle has been reached. As an alternative to this, the blocking can be brought about by the control device.

In order to increase the comfort, provision is made for the control device to have a design that also allows remote controlling so as also to be able to undertake an individual control in addition to an automatic control of the joint. This ensures that the user of the orthopedic device can actively influence the locking state of the joint at all times.

A signal generator can be arranged on the device and displays or announces that the locking device is being opened, and so the user of the orthopedic device is informed during the opening, that is to say during or just before the unlocking of the joint, that the secure locking has been lifted or will be lifted.

A method for controlling an orthopedic device as described above provides for the locking device to be released or blocked as a function of a detected orientation of the upper part and/or the lower part in space. In particular, the locking device is unlocked in the case of a substantially horizontal alignment of the lower part because the assumption is made here that the patient is seated in the case of an embodiment of the orthopedic device as a knee orthosis or as a prosthetic knee joint, and the lower part or the shank should be freely movable.

The angle between upper part and lower part can likewise be detected and the locking device can be unlocked or blocked as a function of the detected angle, wherein a force acting in the lower part can be detected and the locking device can be unlocked or blocked as a function of the detected force. It is advantageous for prosthetic knee joints in particular if a damping resistance is provided in the locking device over a fixed bending range, starting from an extension stop, that allows damped bending and blocks the locking device if the fixed bending angle is exceeded. This affords the possibility of standing with a slightly bent prosthetic knee joint, which corresponds better to the natural appearance. Provision can likewise be made for a warning signal to be emitted before the locking device is released such that there is an acoustic, optical or tactile response from the joint to inform the patient that actual unblocking is taking or has taken place. The unblocking can take place in a continuous fashion by slowly opening the corresponding valves or restrictions, particularly when the locking device is embodied as a hydraulic damper. A timer can prevent immediate blocking of the joint after it has been unlocked, and so a patient has time to prepare for sitting down or bending the joint. The locking device is locked automatically after a prescribed amount of time so that the released position of the joint is not available for a prolonged period of time because it may be the case that although there was active triggering and unblocking of the joint, the patient has forgotten this again. This ensures that the joint automatically locks itself again after a prescribed amount of time if the joint has not been bent by then so that the joint is again in the secured state.

Provision is furthermore made for a bending movement to be locked by the control method during an extension movement of the joint if a fixed joint angle is exceeded, but for a further extension movement still to be possible; this is advantageous in particular for prostheses or orthoses for the lower limbs, but in principle it is also possible to reverse the movement directions if the bent position is to be considered the secure one.

BRIEF DESCRIPTION OF THE DRAWINGS

An exemplary embodiment of the invention is explained in more detail in the following text on the basis of the attached FIGURE. This only FIGURE shows a schematic illustration of an orthopedic device in the form of a prosthetic knee joint.

DETAILED DESCRIPTION

The FIGURE shows a schematic illustration of an orthopedic device in the form of a prosthetic knee joint with a joint upper part 1 having connection means for a prosthesis shaft, and with a joint lower part 2 attached to the joint upper part 1 such that it can pivot. A locking device 3 in the form of a hydraulic damper is attached to the lower part 2 and coupled to the upper part via a piston rod 31. The hydraulic damper 3 is provided with an actuator 4, which opens or closes a valve 5 associated with the hydraulic damper 3 in order to block or unlock the locking device 3. Blocking or unlocking is brought about by opening or closing the valve 5, wherein a slightly longer transition between the "open" and "closed" states can also be implemented in each case in addition to an abrupt opening or closing of the valve 5.

A plurality of sensors 6, 7, 8 coupled to a control device 9 are arranged in the lower part 2, which sensors use the sensor signals as a basis for actuating the actuator 4, which is in the form of a motor or switching element. A position sensor 6 for registering the orientation of the lower part 2 in space is arranged in the lower part 2. Here, it is the orientation relative to gravity that is preferably detected such that the position of the lower part 2 can be determined with ease. A force and torque sensor 7 is arranged in the distal region of the lower part 2 in addition to the position sensor 6 in order to be able to register forces and torques acting within the lower part 2, for example in order to be able to register axial forces that act in the lower part 2, or bending torques that occur during walking or standing. A knee angle sensor 8 is arranged in the region of the upper part 1 and it detects the relative position of the upper part 1, and the connection elements to a human limb connected thereto, with respect to the lower part 2. Using the data from the sensors 6, 7, 8, the control device 9 then calculates whether the locking device is unblocked, locked or switched into a damping mode, which is best suited to the detected situation. Thus, if standing up is expected, extending the upper part 1 relative to the lower part 2 should be allowed, but falling back should be prevented by an appropriate control circuit being blocked in the case of a reversing knee angle and/or a corresponding force within the lower part.

A remote control 10 with a button for entering one or more control commands is illustrated next to the prosthesis, and so in addition to automatic unlocking or blocking of the locking device 3, the latter can also be blocked or unlocked voluntarily by a user. Embodying the actuation device 10 as a remote control is advantageous in that the latter can be positioned anywhere, and so the locking device 3 can be blocked or unlocked independently of the current position and of the abilities of the user.

In addition to an acoustic signal generator 11 for indicating unlocking or immanent unlocking, which is likewise arranged in the lower part 2, it is also possible to arrange a vibration signal generator 12 on the prosthesis so that the prosthesis user is informed that a release is underway or immanent, even in noisy surroundings or if the prosthesis user is hard of hearing.

The illustrated prosthesis allows unlocking even under load; it is likewise possible to bring about locking under load, and so a bending movement can be blocked at all times in order to ensure that the user is as safe as possible. In addition to a remote control 10, an appropriate actuation device can also be arranged on the orthopedic device itself. In addition to an embodiment as a prosthetic knee joint, the orthopedic device can also be provided as a knee joint orthosis or as a prosthesis or orthosis for upper limbs.

The invention claimed is:

1. An orthopedic device with a knee joint, comprising:
an upper part and a lower part mounted thereon such that it can pivot about the knee joint, wherein an upper connection member configured to secure the device to a limb is arranged on the upper part, and which device also has a locking device configured to control a bending movement of the upper part relative to the lower part, wherein the locking device is embodied such that it can actively be actuated by the user of the orthopedic device, wherein a control device is associated with the locking device, is connected to at least one sensor attached to the device and configured to generate a sensor signal, and automatically unlocks or locks the locking device as a function of the sensor signal, wherein the at least one sensor includes an angle sensor for registering an angle between the upper part and the lower part, and a position sensor that determines a spatial orientation of at least the upper part, the joint being locked while the user is standing up and the joint is extended, and the bending movement is locked and an extension movement of the upper part relative to the lower part is released during an entire sit-to-stand movement of the joint if a fixed joint angle is exceeded;
wherein an initial sitting position associated with the sit-to-stand movement being determined when there is an approximate right angle between the upper part and the lower part as measured by the angle sensor, and when the upper part is arranged to coincide with a horizontal plane as measured by the position sensor.
2. The orthopedic device as claimed in claim 1, wherein the at least one sensor includes at least one of a force sensor for registering a force acting in the orthopedic device and a torque sensor for registering a torque acting in the orthopedic device.

3. The orthopedic device as claimed in claim 2, wherein the lower part has an axial force acting therein as measured by the force sensor during the sit-to-stand movement and no axial force acts in the lower part as measured by the force sensor in the sitting position.

4. The orthopedic device as claimed in claim 2, wherein a torque force is present in the knee joint as measured by the torque sensor during the sit-to-stand movement.

5. The orthopedic device as claimed in claim 1, wherein the orthopedic device is designed as a prosthetic knee joint.

6. The orthopedic device as claimed in claim 1, wherein the locking device is a hydraulic damper, which has at least one valve or restriction that can be switched by an actuator, wherein the actuator is connected to the control device.

7. The orthopedic device as claimed in claim 6, wherein a damping element that unlocks in a continuous fashion is associated with the actuator.

8. The orthopedic device as claimed in claim 1, wherein the locking device is designed as a hydraulic damper, which allows damped bending from an extension stop to a fixed bending angle and which blocks further bending once the fixed bending angle has been reached.

9. The orthopedic device as claimed in claim 1, wherein a timing switching element is associated with the control device, the timing switching element delaying unlocking or locking after an appropriate signal.

10. The orthopedic device as claimed in claim 1, wherein the control device has a design that allows remote controlling.

11. The orthopedic device as claimed in claim 1, wherein a signal generator is arranged on the device and displays or announces that the locking device is being opened.

12. The orthopedic device as claimed in claim 1, wherein the locking device is unlocked or locked as a function of a detected spatial orientation of the lower part.

13. The orthopedic device as claimed in claim 1, wherein the locking device is unlocked in the case of an alignment of the lower part within a horizontal plane.

14. The orthopedic device as claimed in claim 1, wherein the angle between upper part and lower part is detected and the locking device is unlocked or locked as a function of the detected angle.

15. The orthopedic device as claimed in claim 1, wherein the at least one sensor includes a force sensor configured to detect a force acting in the lower part, and the locking device is unlocked or locked as a function of the detected force.

16. The orthopedic device as claimed in claim 1, wherein the locking device includes a damping element, and a damping resistance is set in the locking device with the damping element over a fixed bending range, starting from an extension stop, that allows damped bending and locks the locking device if the fixed bending angle is exceeded.

17. The orthopedic device as claimed in claim 1, wherein a warning signal is emitted before the locking device is unlocked.

18. An orthopedic device, comprising:
a knee joint;
an upper part;
a lower part pivotally mounted to the upper part with the joint;
an upper connection member arranged on the upper part and configured to secure the device to a limb;
a locking device configured to control bending movement of the upper part relative to the lower part and be actuated by the user of the orthopedic device;
an angle sensor configured to determine an angle between the upper part and the lower part and generate an angle sensor signal;
a position sensor configured to determine a spatial orientation of at least the upper part in space and generate a position sensor signal;
a control device mounted to one of the upper and lower parts and configured to automatically unlock and lock the locking device in response to the angle sensor signal and the position sensor signal;
wherein the control device locks the locking device while the user is standing up and the joint is extended, and the bending movement is locked and an extension movement of the upper part relative to the lower part is released during an entire sit-to-stand movement of the joint if a fixed joint angle is exceeded;
wherein an initial sitting position associated with the sit-to-stand movement being determined when there is an approximate right angle between the upper part and the lower part as measured by the angle sensor, and when the upper part is arranged to coincide with a horizontal plane as measured by the position sensor.

19. The orthopedic device as claimed in claim 18, further comprising at least one of a force sensor configured to determine a force acting in the orthopedic device and a torque sensor configured to determine a torque acting in the orthopedic device.

20. The orthopedic device as claimed in claim 18, wherein the orthopedic device is designed as a prosthetic knee joint.

21. The orthopedic device as claimed in claim 18, wherein the locking device is a hydraulic damper having at least one valve or restriction that can be switched by an actuator, the actuator being connected to the control device.

* * * * *